United States Patent [19]

Stern et al.

[11] Patent Number: 4,584,271
[45] Date of Patent: Apr. 22, 1986

[54] BACTERIAL REGENERATION APPARATUS AND PROCESS

[75] Inventors: Jay L. Stern, Los Angeles; Herbert W. Spencer, III, Valencia; Alon Lebel, Los Angeles, all of Calif.

[73] Assignee: Joy Manufacturing Company, Pittsburgh, Pa.

[21] Appl. No.: 536,887

[22] Filed: Sep. 28, 1983

[51] Int. Cl.$^4$ .................. C12P 5/02; C12P 3/00; C12N 11/14; C10G 32/00; C12M 1/40; C12M 1/02; C02F 3/00

[52] U.S. Cl. .................. 435/167; 210/611; 210/616; 435/168; 435/176; 435/282; 435/288; 435/316; 435/801; 435/819

[58] Field of Search .............. 435/282, 288, 801, 819, 435/316, 167, 168, 176; 210/611, 616

[56] References Cited

U.S. PATENT DOCUMENTS

| | | | |
|---|---|---|---|
| 3,020,205 | 2/1962 | Jensen | 195/2 |
| 4,124,501 | 11/1978 | Yen et al. | 210/16 |
| 4,127,447 | 11/1978 | Griffith et al. | 210/611 |
| 4,242,448 | 12/1980 | Brown | 435/42 |
| 4,354,937 | 10/1982 | Hallberg | 210/611 |
| 4,519,912 | 5/1985 | Kauffman et al. | 210/611 |
| 4,522,723 | 6/1985 | Kauffman et al. | 210/611 |

FOREIGN PATENT DOCUMENTS 88019 1/1977 Poland.

OTHER PUBLICATIONS

Cork, J. D. et al., "Continuous Disposal of Sulfate by a Bacterial Mutualism" Chap 56 of Development in Industrial Microbiology, vol. 20, published by Soc. for Indus. Micro, 1979, pp. 37–48.

The Sulfate-Reducing Bacteria, J. R. Postgate Cambridge Univ. Press (1979) pp. 1–40.

Cork, Acid Waste Gas Bioconversion–etc., vol. 23, Devel. in Indust. Microbiology (1982) pp. 379–387.

Cork et al., *Chlorobium limicola* Forma thiosulfatophilum etc., Mar. 1983 Applied and Environmental Microbiology, pp. 913–918.

Visible Light Cleaves Hydrogen Sulfide, Science Chemical & Engineering News, Jul. 27, 1981, pp. 40 & 42.

Parnell, Claus-UCAP (integrated UCAP) Sulfur Recovery, TVA "Ammonia From Coal Symposium", May 9, 1979.

Parnell, Latest Devel. in Sulfur Recovery Units, Amer. Instit. Chem. Eng. & Amer. Chem. Soc., Mar. 30, 1979.

Parnell, Differences in Design of Claus Units for Various Applications, AIChE Meeting 4/9/81.

Kelly et al., Pilot Plant Eval. of H$_2$S, COS and CO$_2$ Removal From Crude Coal Gas by Refrigerated Methanol (undated).

Matson, et al., Progress on the Selective Removal of H$_2$S From Gasified Coal etc., I & EC Process Des. & Devel., vol. 16, pp. 370–376 (7/1977).

Riesenfeld et al., Acid Gas Removal Processes Compared, vol. 41, No. 4, Hydrocarbon Processing & Petroleum Refiner, pp. 123–127 (1962).

*Primary Examiner*—David M. Naff
*Assistant Examiner*—Louanne C. Krawczewicz
*Attorney, Agent, or Firm*—Arnold B. Silverman

[57] ABSTRACT

Apparatus and a method are disclosed for reducing sulfate contained within a flowable material to hydrogen sulfide by the use of two stages of reaction. The flowable material is deoxygenated and then introduced into a first reactor which contains a sulfate reducing bacteria such as a Desulfovibrio or Desulfotomoculum. Hydrogen sulfide is removed from the first reactor and the remaining portion of the flowable material is subjected to a separating action to produce a supernatant component and a sludge component. The sludge component is reintroduced to the first reactor which is generally devoid of packing or support and the supernatant is introduced into a second reactor which is preferably in the nature of a supported film reactor. Mixed products including carbonate may be removed from the first reactor. The second reactor also contains anaerobic sulfate reducing bacteria. Hydrogen sulfide, low sulfate water and carbonates may be withdrawn from the second reactor. The hydrogen sulfide may be oxidized to produce free sulfur.

34 Claims, 1 Drawing Figure

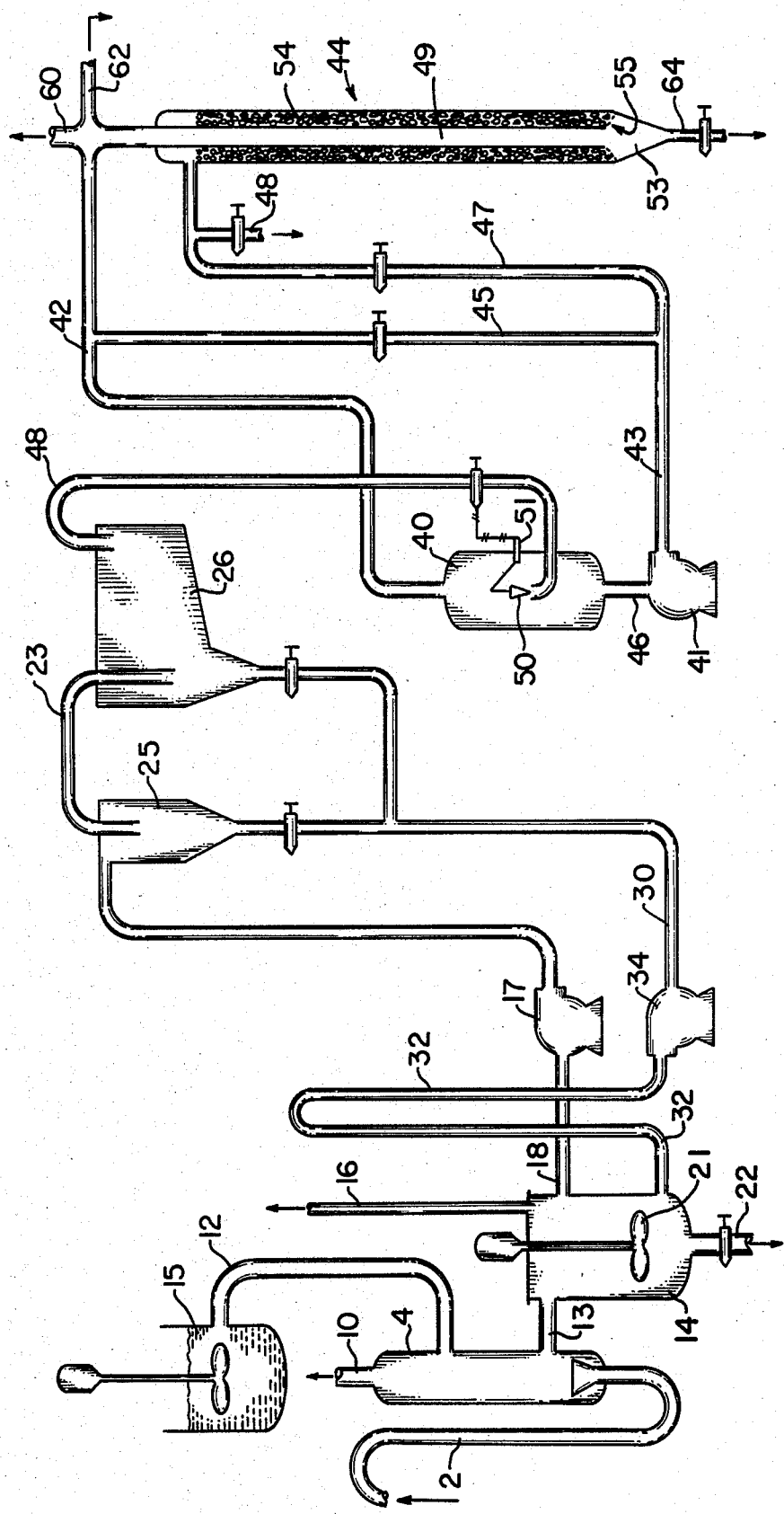

BACTERIAL REGENERATION APPARATUS AND PROCESS

FIELD OF THE INVENTION

The present invention relates to apparatus and a method for reducing sulfate contained within a flowable material by the use of sulfate reducing bacteria and, more specifically, is directed toward apparatus and methods suitable for purification of such flowable materials while simultaneously recovering usable products.

DESCRIPTION OF THE PRIOR ART

As a result of environmental controls it has become necessary and desirable to clean flue gas prior to discharge in order to minimize air pollution. Such cleaning frequently takes the form of wet scrubbers which remove gaseous sulfur from the air and convert the same into sulfites or sulfates which appear in the waste water from the scrubber operation. In order to avoid environmental violations and potential health hazards which might occur were the sulfite and sulfate containing waters discharged, it has become necessary to store such wastes as dewatered solids in landfills, or in suspensions and thixotropic slurries in ponds or lagoons. Storage and dewatering operations are non-economic and undesirable.

It has been known to recover sulfur from sulfate containing ores by various means including the use of bacteria to reduce the sulfate to sulfide. See, for example, Postgate, "The Sulfate-Reducing Bacteria", pp. 1-40.

It has been suggested to treat oil shale retort water through use of anaerobic bacteria of the Desulfovibrio family to reduce sulfate ions to sulfide with subsequent reoxidation to sulfate and recovery of industrial grade water. See U.S. Pat. No. 4,124,501.

It has also been suggested to reduce sulfate to hydrogen sulfide through use of Desulfovibrio bacteria and to subsequently oxidize the hydrogen sulfide to produce sulfur. See U.S. Pat. No. 3,020,205. As with other prior art teachings, this patent teaches the use of a single step, single vessel for production of sulfide. The disclosure has not quantified or defined process parameters and does not contemplate production of additional useful products such as carbonates.

U.S. Pat. No. 4,242,448 discloses the treatment or scrubbing of stack gases from a fossil fuel burning operation wherein Desulfovibrio bacteria are employed to reduce sulfate ions to hydrogen sulfide and simultaneously or serially to employ bacteria of the genus Beggiatoa to oxidize the hydrogen sulfide to form sulfur. The effluent is said to be recycled to the scrubber. This disclosure requires simultaneous use of anaerobic bacteria (Desulfovibrio) and aerobic bacteria (Beggiatoa) in a stagnant two tier arrangement to accomplish these two objectives.

Polish Pat. No. 88019 discloses the use of a waste solution of ammonium sulfate in a process wherein microbiological decomposition of ammonium sulfate to hydrogen sulfide and ammonium carbonate is effected with the use of *Desulfovibrio desulfuricans* in the presence of sewer liquid nutrient. Ammonium carbonate is said to be returned to the gas cleaning process which generated the waste solution.

In spite of these prior teachings, reduction to practice has not been feasible. There remains a clear and substantial need for an industrial scale system capable of efficiently and economically producing carbonates of alkaline earths and alkali metals, reduced sulfur compounds, biomass and industrial quality water from suspended and solubilized sulfates of these earths and metals present in waste streams, by means of sulfate reducing bacteria disposed in specifically designed reaction vessels to which a supply of nutrients is fed and from which oxygen entry is resisted.

SUMMARY OF THE INVENTION

The present invention has met the above-described need by providing a method and associated apparatus for extracting from waste streams any sulfates as sulfides, while producing low sulfate water, biomass and carbonates. All of this is accomplished in an efficient and economical manner which employs two distinct stages and reactors, each with associated components and materials.

It is an object of the present invention to provide an apparatus and associated continuous method for efficient and rapid conversion of sulfates contained within a flowable material into sulfides which, if desired, may be oxidized to produce free sulfur.

It is yet another object of the invention to provide such a system wherein anaerobic sulfate reducing bacteria are employed in the reaction vessels and are provided with suitable conditions for maximum growth to thereby promote their sulfate reducing action.

It is a further object of the present invention to provide such a system which is adapted to receive as a source of sulfate, the flowable material obtained from stack gas scrubbers installed on fossil fuel combustors.

It is yet another object of the invention to provide means for producing alkali metal and/or alkaline earth carbonates obtained from the flowable material.

It is a further object of the present invention to provide such a system which will produce low sulfate water.

It is a further object of the invention to provide such a system which is designed to minimize capital investment required to produce an effective system.

It is a further object of the invention to provide a system which is adapted to receive as a source of sulfate dissolved and slurried effluent formed from waste alkali metal (or alkaline earth) sulfate, sulfite, thiosulfate or thiosulfite or similar materials, which can include waste sulfuric acid.

These and other objects of the invention will be more fully understood from the following description of the invention on reference to the illustration appended hereto.

BRIEF DESCRIPTION OF THE DRAWING

The FIGURE is a schematic illustration of one form of system of the present invention.

DESCRIPTION OF THE PREFERRED EMBODIMENTS

In the absence of an express and specific indication to the contrary in connection with a particular usage herein, the following terms will be defined as follows:

(a) "sulfate" means any of the anions of alkali metals or alkaline earths bearing sulfur in an oxidized form, including but not limited to, sulfate ($SO_4^=$), sulfite ($SO_3^=$), thiosulfate, thiosulfite ($S_2O_3^=$), bisulfate ($HSO_4^-$) or bisulfite ($HSO_3$);

(b) "flowable material" means any true solution, slurry or aqueous suspension of sulfate containing wastes;

(c) "alkali metal" means any element in group 1a of the periodic table and in a preferred embodiment is restricted to sodium and potassium;

(d) "alkaline earth" means any element in group 2a of the periodic table and in a preferred embodiment is restricted to magnesium and calcium;

(e) "slug reactor" means an unbaffled or unpacked closed tank of given dimensions in which sulfate reduction occurs without a meaningful bacterial substrate other than solids introduced concurrently with soluble sulfate; and (f) "film reactor" means a closed vessel offering a substrate for bacterial attachment and growth.

Referring now in greater detail to the FIGURE, there is shown a schematic illustration of a preferred two-stage system of the present invention.

The sulfate containing flowable material, such as the waste effluent from a flue gas scrubber is introduced into the system through conduit 12 from a holding/mixing tank 15. The deoxygenation vessel 4 receives the effluent and, also receives an oxygen displacing gas through conduit 2. This gas may, for example, be nitrogen, flue gas or hydrogen sulfide. The deoxygenation gas serves to remove oxygen from the flowable material with the oxygen and deoxygenation gas emerging from the vessel 4 through discharge outlet 10. The deoxygenated flowable material then passes through conduit 13 to slug reactor 14.

The slug reactor 14, a suspended growth unit, in the form shown has an elongated construction and is preferably composed of reinforced plastic, steel, concrete or another suitable material any of which may be lined with a material which is inert with respect to the flowable material to be treated. Disposed within the slug reactor 14 are a suitable sulfate reducing bacteria and an appropriate nutrient to stimulate growth of the bacteria. The bacteria may be introduced into the system by any convenient means either upstream of the reactor 14 or directly into the reactor 14 or both. The nutrients may be blended in a ratio dependent upon the sulfate content of the flowable material and estimated usable nutrients disposed in the reactor 14. A portion of the sulfate in the flowable material is reduced to hydrogen sulfide which is withdrawn from the slug reactor 14 through discharge outlet 16. Mixed, solid products suspended in water to the consistency of a slurry are removed through sludge drain 22. The composition of these mixed products may include inert materials conveyed into the slug reactor, living and dead bacteria ("biomass"), precipitated carbonates and unreacted sulfates. The aqueous liquor which suspends these materials may be saturated with them. Inert materials will typically be silicate and aluminate compounds arising from any fly ash mixed with the influent sulfates. Heavy metals, if present, can be expected to appear in the mixed products.

The stream of mixed products will be separated after leaving the slug reactor 14. Carbonates will be returned to the flue gas desulfurization process, biomass may be dewatered and burned and unusable materials will compact easily to form landfill. It is expected that the bulk of such material will be relatively small compared to the volume of carbonates and subsequently produced sulfur. Hydrogen sulfide, or other sulfides may be stripped from the mixed product stream by ordinary industrial means and used to recover sulfur.

The flowable material with a portion of the sulfate bacterially metabolized to sulfide is withdrawn through outlet conduit 18 by pump 17. The quantity of solid sulfates in the stream withdrawn through conduit 18 is less than that in the stream which enters through conduit 13. In order to facilitate achieving homogeniety of the material in the slug reactor 14 and improved efficiency of chemical action, agitating means, such as a low shear stirrer 21 which may be mechanically driven by a motor disposed exteriorly of the reactor is provided.

In general, no support for the bacteria will be provided in slug reactor 14 apart from that offered by the undissolved solids. As the bacteria metabolize sulfates dissolved in the flowable material, more solids will enter solution and the surface area available to the bacteria will diminish. Additional flowable material is then admitted to slug reactor 14 from tank 15 or recycle conduit 32 to maintain a desired concentration of non-dissolved solids.

Among the preferred sulfate reducing bacteria are those falling within the genus Desulfovibrio and the genus Desulfotomaculum. Among the specifically preferred Desulfovibrio species are *desulfuricans, vulgarus, salexigens, africanus* and *gigas*. The bacteria employed may either be a pure strain of one type or a mixture of two or more types.

It is preferred that the process being performed in the slug reactor 14 be performed at a temperature of about 15° C. to 40° C., with about 30° C. to 37° C. being preferred. The internal pressure of the reactor 14 may be atmospheric.

It is preferred that the pH of the material in the slug reactor 14 be about 6.0 to 8.0, with about 6.8 to 7.5 being preferred.

The invention contemplates providing a suitable source of nutrient media for bacterial growth within slug reactor 14. The nutrient media is preferably present at its solubility limit in order to maximize efficiency. Lactic acid which may be provided in the form of dairy byproducts or wastes, such as sour milk, whey stream or washdown from cattle is a preferred carbon source. Other compounds, such as pyruvate, butyrate and four-carbon fatty acids are also suitable. Additional sources of these materials include residues as from the pulp and paper industry, domestic and municipal sewage and agricultural wastes. Combinations of these materials may be employed.

As the bacteria employed are anaerobic, it is important that not only the deoxygenation stage effectively remove substantially all of the oxygen contained in the waste as introduced, but that the slug reactor 14 be suitably sealed to resist entry of oxygen.

Referring once again to the FIGURE, it is seen that the flowable material is transported from the slug reactor 14 to the separators 25 and 26 in conduit 18. In the separators 25 and 26 the flowable material is separated into a supernatant component and a sludge component. The separators 25 and 26 may take the form of any conventional material separating equipment such as a centrifugal separator or sedimentation tank, for example. The supernatant component is removed through conduits 23 and 48 and the sludge component is removed through discharge conduit 30. The sludge component is delivered through conduits 30 and 32 by means of pump 34 to the slug reactor 14 for additional processing by bacterial action. Conduits 23 and 48 transport the supernatant emerging from the separators 25 and 26 to holding tank 40 from which it will pass to the second stage of operation.

The mixture emerges from the holding tank 40 through conduit 46, and by means of pump 41 is introduced by way of conduits 43 and 47 into the film reactor 44, an attached growth unit, which is sealed to resist entry of oxygen. Conduit 48 serves as a sample port and may also function as a vent, if desired. Bypass conduit 45 which may be used for backflushing has a valve and connects conduit 42 with conduit 43.

The interior of the film reactor 44 is provided with a means to support the bacteria. In the embodiment shown, a packing material 54 disposed within an annulus serves as support for the anaerobic sulfate reducing bacteria. Among the preferred materials for this purpose is a material selected from the group consisting of crushed glass, glass beads, plastic particles, ceramic particles, plastic or glass tubes, pumice, sand and gravel. The packing means will generally be of such size and shape as to provide a porosity or an interstitial volume of at least about 20 to 60 percent of the volume of the portion of the film reactor 44 which is occupied by the packing material, and preferably at least about 26 to 40 percent. The interstitial voids of such packing means will generally be large enough to resist rapid plugging of the packing material by biomass or precipitated product, yet small enough to allow the containment vessel to be reasonably sized. In a preferred embodiment, the voids are not smaller than about 100 cubic microns nor larger than about ⅛ cubic inch. In general, it is preferred that solids not be intentionally concurrently introduced into the film reactor 44 with soluble sulfates.

In the form illustrated the sulfate containing flowable material will, under the influence of pump 41, be introduced into film reactor 44 and be caused to pass over the column packing thereby causing the material to interact with the anaerobic bacteria. It will be appreciated that, in general, in the slug reactor 14 enhancement of sulfate reduction is achieved through agitation, whereas enhancement of sulfate reduction is achieved in the film reactor 44 by contacting a high density of bacteria on the column packing. Also, as a result of the packing material serving as a support for the bacteria and by providing suitable nutrient media within the film reactor 44 (either by direct introduction or by carryover from the slug reactor or both), such as the type described hereinbefore, the opportunity for bacterial growth is maximized. It will be appreciated that the absence of any permanent support for the bacteria in the slug reactor 14 will cause bacteria and nutrient material to be transported with the supernatant to the film reactor 44. Thus, nutrient may flow into the film reactor 44 from the slug reactor 14 or be supplied directly into film reactor 44 or both.

In the form illustrated, the film reactor 44 has an axial tube 49 around which the packing material is positioned. A perforated plate 55 permits gas and liquid flow therethrough into chamber 53 while resisting passage of packing material therethrough. Chamber 53 underlies plate 55.

In order to maximize recovery achieved in the second stage of the system, conduit 42 recycles a portion of the processed flowable material from the film reactor 44. The holding tank through suitable valving such as level control 51 and level control valve 50 will effect the desired proportionate mixing of the supernatant component and the recycled material. In general, the ratio of supernatant component to recycled material will be about 0.1 to 2.0:1 and preferably about 0.5:1 to 1.0:1.

Referring still to the film reactor 44, it is seen that the hydrogen sulfide will be withdrawn through chamber 53 and tube 49 as an overhead product through conduit 60. Water low in sulfate will be withdrawn through conduit 62 by any suitable means. Carbonates as well as other products such as biomass, for example will be withdrawn through chamber 53 and lower outlet 64. Soluble organic metabolic products and inorganic compounds will be withdrawn both through conduit 60 and lower outlet 64.

In general, it will be preferred to maintain the internal temperature of the film reactor 44 at a temperature of about 15° C. to 40° C., with about 30° C. to 37° C. being preferred. The pH should be maintained at about 6.0 to 8.0 and preferably 6.8 to 7.5. The internal pressure of the film reactor may be at about atmospheric pressure.

It will be appreciated that by the above-described system and associated method, two independent stages of processing are achieved through the use of the slug reactor 14 and the film reactor 44, with the supernatant component of the output of the slug reactor 14 serving to provide input to the film reactor 44.

With regard to sizing of the system, this will be dependent, to a great extent, on the nature of the environment in which the system will be placed and the primary objectives. For example, if the system were to be installed in association with a wet scrubbing process used in flue gas desulfurization, one would consider the needs of the process for the low sulfate water which would be produced by the film reactor, as well as the regenerative carbonate aspects of the system. In addition, in sizing the reactors 14 and 44 one would have to consider the desired dwell time for optimum chemical reactions and the flow rates which might be achieved. In general, for most uses, it will be referred that the interior volume of the slug reactor 14 be about 10 to 30 times the interior volume of the film reactor 44.

The following sets forth the chemical reactions which are presently believed to occur in the bacterial reduction of sulfates to hydrogen sulfide such as occurs in the first stage of the present system in the slug reactor 14 and as occurs in the second stage in film reactor 44.

Anaerobic sulfate reducing bacteria, such as Desulfovibrio species, in the presence of an appropriate carbon-based nutrient (such as a salt of lactic acid) decouple the oxygen from sulfur in sulfate compounds and transfer it to hydrogen thereby forming water. The lactate is metabolized to carbon dioxide, a salt of acetic acid and additional biomass. The hydrogen made available from water reacts with the reduced sulfur moiety to form hydrogen sulfide gas. The descriptive reactions are thought to be as follows.

Initially, sulfates, such as gypsum, (CaSO$_4$) dissolve in water resulting in the disassociation shown in equation (1).

$$CaSO_4 \rightarrow Ca^{+2} + SO_4^{-2} \tag{1}$$

Dissolution of the carbon source, such as sodium lactate, is shown in equation (2).

$$CH_3CH(OH)COONa \rightarrow CH_3CH(OH)COO^- + Na^+ \tag{2}$$

The anaerobic bacteria, such as Desulfovibrio, produce sulfur anions and oxygen from the reduction shown in equation (3) with "B" indicating bacterial metabolism.

$$2CH_3CH(2OH)COO^- + SO_4^{-2} \xrightarrow{B} 2CH_3COO^- + 2CO_2 + 2H_2O + S^{-2} \quad (3)$$

Disassociation of water is shown in equation (4).

$$2H_2O \rightarrow 2OH^- + 2H^+ \quad (4)$$

The reaction of calcium cation with hydroxyl anion is shown in equation (5).

$$Ca^{+2} + 2OH^- \rightarrow Ca(OH)_2 \quad (5)$$

Absorption of $CO_2$ in hydroxide solution is shown in equation (6).

$$Ca(OH)_2 + CO_2 \rightarrow \downarrow CaCO_3 + H_2O \quad (6)$$

with calcium carbonate being precipitated.

The reaction of acetate ion with available cation is shown in equation (7).

$$2CH_3COO^- + 2Na^+ \rightarrow 2CH_3COONa \quad (7)$$

The production of hydrogen sulfide is shown in equation (8).

$$2H^+ + S^= \rightarrow \uparrow H_2S \quad (8)$$

The material desired to be produced from a sulfate reduction process may be a nominally insoluble carbonate, such as calcium carbonate. The sulfate precurser may also be of low solubility. The present invention addresses this fact by use of a two-stage process which will allow low solubility sulfates to be processed with the precipitation of insoluble carbonates. The solubility of calcium sulfate in water is about 0.2 gm/100 ml, and its density is around 2.6 gm/cc. For solubility, the ratio of water to calcium sulfate (by weight) is:

$$\frac{(2.6 \text{ gm/cc})}{(0.2 \text{ gm/100 cc})} = 1300:1$$

A great amount of water would be necessary to process even a modest amount of calcium sulfate, if all sulfate were dissolved simultaneously. If, on the other hand, a defined quantity of water is used, sulfate will dissolve up to its solubility limit. The remainder of the sulfate will consist of undissolved solids. As bacterial action reduces the dissolved sulfate concentration by conversion into sulfide, more sulfate will dissolve. Thus, the concentration of sulfate will remain at or near saturation until the last of the undissolved sulfate enters solution. Then, and only then, will the concentration of dissolved sulfate diminish. The rate of bacterial metabolism will remain constant (assuming free supply of carbon-based and other essential nutrients) until the sulfate concentration diminishes. Then, the conversion of sulfate to sulfide slows.

The "two-stage" concept of the present invention recognizes these physical and biological limitations. Consequently, smaller vessels can be used and still achieve at least as high a production of sulfide and carbonate as would occur in a basin wherein all sulfates are dissolved simultaneously. The "slug reactor" is not intended to reduce the concentration of sulfur in the aqueous phase; carbonate product will accumulate, and sulfide will be evolved, but the liquor will be saturated with respect to sulfate. The bottom product from the slug reactor will consist of carbonates mixed with unreduced sulfates, heavy metal sulfides, biomass and so forth.

The aqueous supernatant is conveyed, in a volume dictated by the requirements of the end user, to a separation vessel where the undissolved solids are removed and returned to the slug reactor. After separation, the clarified liquor, which may be supplemented with fresh carbon-based and other nutrients, is conveyed to a film reactor. The film reactor is a tank or vessel containing a support material such as crushed glass, plastic, gravel, sand and the like. Onto this supporting media sulfate reducing bacteria adhere and multiply and eventually form a film covering the support. Their concentration is very high, compared to the population elsewhere in the system. As sulfate-laden liquor passes over this bacterially populated support, their metabolism produces carbonate and sulfide.

Solid carbonates will gather within the void volume of the packing and will also be conveyed to the low point of the reactor, i.e. adjacent to outlet 64. Design optimization intends to forstall bed plugging as long as possible and to facilitate back-washing for the removal of carbonate and biomass.

The carbonate emerging from the supported film reactor will, in general, be contaminated only by biomass. Separation, which may be accomplished by conventional processes, is effected to yield a carbonate product sufficiently pure for industrial processes, such as scrubbing flue gases for air pollution control.

The low sulfate water co-produced will be rich in acetate, a byproduct of lactate metabolism. Such acetate is ideal for further processing by conventional anaerobic biological treatment (by means of methane producing bacteria such as Methanobacter) into methane gas, $CH_4$.

Even though a serial arrangement for the slug reactor, separation vessel and film reactor were discussed as the preferred embodiment, the specific requirements of a given installation will dictate the precise arrangement, shape and size of the equipment. Thus, additional reactors of either type and/or additional separators could be considered in parallel or sequentially without substantially altering the "two-stage" concept of the present invention. In a sequential reactor arrangement, especially involving the film reactor, two or more vessels may be desirable to most advantageously reduce sulfate to sulfide and carbonate. Factors prompting consideration of one or more such additional vessels include the need for supplemental nutrient, optimum reactor height-to-volume ratio, optimum retention time, ease of product recovery and bed depth, and the like.

It is not contemplated that a 1:1 ratio of slug reactor to film reactor to separator will necessarily be maintained in a functioning sulfate reduction plant. Economics, with respect to capital investment and operating costs would be the primary determinant in such case.

It will be appreciated that the sulfate source employed in the present invention may be obtained from numerous sources, including but not limited to coal, shale and biomass gasifiers, sulfuric acid plants, magnethydrodynamic power generators, chemical and petroleum refining plants, cement manufacturing operations, flue gas scrubbing, mixing of dissimilar ocean waters, pulp and paper mills and other industrial processes.

As an optional additional advantageous feature of the present invention, it is contemplated that the hydrogen sulfide generated in the process and through the apparatus of the present invention may be converted to free sulfur. This can most advantageously be accomplished through the preferred use of the Claus process, although other known processes may be employed. See, for example, Cork, D. J. "Acid Waste Gas Bioconversion—An Alternative to the Claus Desulfurization Process" Developments in Industrial Microbiology, Volume 23, Chapter 34, 1982; Cork, D. J. et al, "Chlorobium Limicola Ferma Thiosulfatophilum: Biocatalyst in the Production of Sulfur and Organic Carbon from a Gas Stream Containing $H_2O$ and $CO_2$" Applied Environmental Microbiology, Volume 45, No. 3, p. 913–918, March 1983; Visible Light Cleaves Hydrogen Sulfide," *Chemical and Engineering News*, July 27, 1981; Parnell, D. C., "Claus-UCAP (Integrated UCAP) Sulfur Recovery" at TVA "Ammonia from Coal Symposium," May 9, 1979, Muscle Shoals, Alabama; Parnell, D. C. "Latest Developments in Sulfur Recovery Units" at 26th Annual Joint Technical Meeting of the AIChE and ACS. Mar. 30, 1979, Port Arthur, Tex.; Parnell, D. C., "Differences in Design of Claus Units for Various Applications" at AIChE Spring National Meeting, April 9, 1981; Kelly, R. M. et al., "Pilot Plant Evaluation of $H_2S$, COS, and $CO_2$ Removal from Crude Coal Gas by Refrigerated Methanol"; Matson, S. L. et al., "Progress on the Selective Removal of $H_2S$ from Gasified Coal"; Using an Immobilized Liquid Membrane," I & EC Process Design and Development, Vol. 16, page 370, July, 1977; and Riesenfeld, F. C. and Blohm, C. L., "Acid Gas Removal Processes Compared Hydrocarbon Processing and Petroleum Refiner, Vol. 41, #4, page 123–127, April, 1962.

It will be appreciated that the present invention provides a unique apparatus and process for multi-stage conversion of sulfates to hydrogen sulfide along with production of low sulfate water, carbonates and other materials. All of this is accomplished in a closed system which permits the use of specific anaerobic bacteria which in one reactor is permitted to effect reduction in substantially unsupported condition and in another reactor in supported condition. Suitable nutrient media are provided in order to maximize growth rates of the bacteria and efficiency of operation of the system. Subsequently, oxidation of the hydrogen sulfide to produce free sulfur and use of the carbonates and low sulfate water are contemplated.

While the preferred process of the invention involves a continuous, as distinguished from batch process, the materials will be retained in the reactors 14 and 44 for a period of time which will maximize process efficiency. While the time periods may vary substantially with different conditions, in one experiment, effective results were obtained with a 24 hour retention period in the slug reactor and about 1–3 hour retention period in the film reactor 44.

Whereas particular embodiments of the invention have been described above for purposes of illustration, it will be appreciated by those skilled in the art that numerous variations of the details may be made without departing from the invention as described in the appended claims.

We claim:

1. Apparatus for reducing sulfate contained within a flowable material comprising
   deoxygenation means for removing oxygen from a flowable material containing sulfate,
   slug reactor means for processing said deoxygenated flowable material to reduce at least a portion of said sulfate to sulfide,
   anaerobic bacteria means disposed in said slug reactor means for reducing at least a portion of said sulfate,
   said anaerobic bacteria including at least one microorganism strain selected from the group consisting of *Desulfovibrio* and *Desulfotomaculum*,
   separation means for receiving flowable material from said slug reactor and separating the same into supernatant containing sulfate and sludge components,
   means for delivering said sludge component to said slug reactor means,
   film reactor means for receiving and processing said supernatant component to reduce at least a portion of said sulfate to sulfide,
   means for delivering said supernatant component to said film reactor means,
   said slug reactor means and said film reactor means each being sealed to resist entry of oxygen,
   anaerobic bacteria means disposed in said film reactor means for reducing at least a portion of the sulfate contained in said supernatant, and
   at least one of said slug reactor means and said film reactor means containing nutrient media for sustaining growth of said anaerobic bacteria.
2. The apparatus of claim 1 including
   agitating means for maintaining the contents of said slug reactor in an agitated state during operation of said apparatus.
3. The apparatus of claim 2 wherein
   said agitating means includes stirrer means.
4. The apparatus of claim 1 wherein
   said anaerobic bacteria include at least one microorganism species selected from the group consisting of *Desulfovibrio desulfuricans*, *Desulfovibrio vulgarus*, *Desulfovibrio salexigens*, *Desulfovibrio africanus* and *Desulfovibrio gigus*.
5. The apparatus of claim 3 including
   said film reactor means having bacterial support means.
6. The apparatus of claim 5 wherein
   said bacterial support means includes a material selected from the group consisting of crushed glass, glass beads, plastic particles, ceramic particles, plastic tubes, glass tubes, pumice, sand and gravel.
7. The apparatus of claim 6 including
   said support means being of such size and shape as to provide an interstitial volume of about 20 to 60 percent of the volume of the portion of said film reactor means occupied by said bacterial support means.
8. The apparatus of claim 7 including
   first hydrogen sulfide collecting means operatively associated with said slug reactor means for withdrawing hydrogen sulfide therefrom, and
   second hydrogen sulfide collecting means operatively associated with said film reactor means for withdrawing hydrogen sulfide therefrom.
9. The apparatus of claim 8 including
   said film reactor means having means for removal of low sulfate water.
10. The apparatus of claim 9 including holding tank means for receiving said supernatant component and recycled supernatant from said film reactor means.

11. The apparatus of claim 10 including delivery means for delivering said supernatant component and said recycled supernatant from said holding tank means to said film reactor means.

12. The apparatus of claim 9 including said slug reactor having carbonate discharge means.

13. The apparatus of claim 11 including said delivery means having pump means.

14. The apparatus of claim 14 including said film reactor means having carbonate discharge means.

15. The apparatus of claim 1 including said deoxygenation means having a vessel with inlet and discharge means for receipt and discharge of said flowable material,
said deoxygenation vessel having deoxygenation gas inlet means and gas outlet means, and
said flowable material discharge means of said deoxygenation means being in communication with said slug reactor means.

16. The apparatus of claim 1 including said slug reactor having an interior volume equal to about 10 to 30 times the interior volume of the film reactor means.

17. The apparatus of claim 1 including said slug reactor means being substantially devoid of support means for said bacteria apart from solids contained within said flowable material.

18. The apparatus of claim 1 including means for converting said sulfide to free sulfur.

19. A method for reducing sulfate contained within a flowable material comprising
deoxygenating a flowable material containing sulfate,
introducing said deoxygenated flowable material into a first reactor means, sealed to resist entry of oxygen, containing sulfate reducing bacteria,
employing as said sulfate reducing bacteria at least one microorganism selected from the group consisting of Desulfovibrio and Desulfotomaculum,
reducing at least a portion of said sulfate to hydrogen sulfide,
withdrawing said hydrogen sulfide from said first reactor,
withdrawing said processed flowable material from said first reactor,
separating of said processed flowable material into supernatant containing sulfate and sludge components,
delivering said sludge component to said first reactor,
delivering said supernatant component to a second reactor means, sealed to resist entry of oxygen, containing sulfate reducing bacteria,
reducing at least a portion of said sulfate to hydrogen sulfide,
withdrawing said hydrogen sulfide from said second reactor, and
withdrawing low sulfate water from said second reactor.

20. The method of claim 19 including agitating the contents of said first reactor during the processing of said flowable material.

21. The method of claim 20 including employing stirrer means to agitate said contents.

22. The method of claim 21 including employing as said sulfate reducing bacteria at least one microorganism species selected from the group consisting of *Desulfovibrio desulfuricans, Desulfovibrio vulgarus, Desulfovibrio salexigens, Desulfovibrio africanus* and *Desulfovibrio gigus.*

23. The method of claim 22 including providing bacterial support means in said second reactor means.

24. The method of claim 23 including providing as said bacterial support means which is a material selected from the group consisting of crushed glass, glass beads, plastic particles, ceramic particles, plastic tubes, glass tubes, pumice, sand and gravel.

25. The method of claim 24 including placing said support means in said second reactor means so as to provide an interstitial volume of about 20 to 60 percent of the volume of the portion of said second reactor means occupied by said support means.

26. The method of claim 25 including admixing said supernatant component with recycled flowable material received from said second reactor means prior to introducing said supernatant component into said second reactor means.

27. The method of claim 26 including withdrawing hydrogen sulfide, low sulfate water and carbonates from different discharge outlets of said second reactor means.

28. The method of claim 21 including maintaining said first reactor means at a temperature of about 15° to 40° C. during said process.

29. The method of claim 28 including maintaining the pH of said first reactor at about 6.0 to 8.0 during said process.

30. The method of claim 29 including providing nutrient media to at least one of said reactors.

31. The method of claim 29 including maintaining the temperature of said second reactor means at about 15° to 40° C. during said process.

32. The method of claim 31 including maintaining the pH of said second reactor means at about 6.0 to 8.0 during said process.

33. The method of claim 32 including oxidizing hydrogen sulfide obtained through said process to free sulfur.

34. The method of claim 31 wherein said low sulfate water contains acetate and including converting at least a portion of the acetate to methane gas by biological treatment with a methane producing bacteria.

* * * * *